(12) United States Patent
Elangovan et al.

(10) Patent No.: US 10,725,550 B2
(45) Date of Patent: Jul. 28, 2020

(54) METHODS AND APPARATUS FOR RECOGNITION OF A PLURALITY OF GESTURES USING ROLL PITCH YAW DATA

(71) Applicant: Nod, Inc., Santa Clara, CA (US)

(72) Inventors: Anusankar Elangovan, San Francisco, CA (US); Harsh Menon, Cupertino, CA (US)

(73) Assignee: NOD, INC., Santa Clara, CA (US)

( * ) Notice: Subject to any disclaimer, the term of this patent is extended or adjusted under 35 U.S.C. 154(b) by 897 days.

(21) Appl. No.: 14/637,352

(22) Filed: Mar. 3, 2015

(65) Prior Publication Data

US 2015/0241985 A1 Aug. 27, 2015

Related U.S. Application Data

(63) Continuation-in-part of application No. 14/591,878, filed on Jan. 7, 2015, now Pat. No. 10,338,678.
(Continued)

(51) Int. Cl.
*G06F 3/01* (2006.01)
*G06F 3/044* (2006.01)
(Continued)

(52) U.S. Cl.
CPC ............ *G06F 3/017* (2013.01); *G06F 1/3259* (2013.01); *G06F 3/011* (2013.01); *G06F 3/014* (2013.01); *G06F 3/016* (2013.01); *G06F 3/044* (2013.01); *G06K 9/00355* (2013.01); *G06K 9/00375* (2013.01); *A61B 5/1123* (2013.01); *A61B 2562/0219* (2013.01); *Y02D 10/155* (2018.01)

(58) Field of Classification Search
CPC .......... G06F 3/01; G06F 3/044; G06F 3/0416; G06F 3/005; G06F 3/0412; G06F 3/014; G06F 3/015; G06F 3/016; G06F 3/0346; G06F 3/012; G06F 1/163; G06F 3/017; G06F 3/011; G06F 3/0304; A61B 5/681; G06K 9/00375; G06K 9/00355; G06K 9/00389; G06K 9/00335; G06K 9/00342; G06K 9/544
USPC ........................................................ 345/156
See application file for complete search history.

(56) References Cited

U.S. PATENT DOCUMENTS 6,044,297 A * 3/2000 Sheldon ............. A61N 1/36542
600/585
6,305,221 B1 * 10/2001 Hutchings .............. A63B 24/00
73/488
(Continued)

FOREIGN PATENT DOCUMENTS

WO 2013/104681 7/2013

OTHER PUBLICATIONS

Full Search Report dated Jun. 1, 2015 in corresponding PCT/US15/010533.
(Continued)

*Primary Examiner* — Dismery Mercedes
(74) *Attorney, Agent, or Firm* — Pillsbury Winthrop Shaw Pittman LLP

(57) ABSTRACT

Described are apparatus and methods for reconstructing a plurality of gestures using roll pitch and yaw data, typically in combination with data for recognition of start and/or stop portions of the gesture using an auxiliary sensor, such as a capacitive touch sensor or a MEMS sensor.

20 Claims, 18 Drawing Sheets

Related U.S. Application Data

(60) Provisional application No. 61/924,682, filed on Jan. 7, 2014.

(51) Int. Cl.
    *G06K 9/00*     (2006.01)
    *G06F 1/3234*     (2019.01)
    *A61B 5/11*     (2006.01)

(56) References Cited

U.S. PATENT DOCUMENTS

| | | | | |
|---|---|---|---|---|
| 6,515,669 | B1* | 2/2003 | Mohri | G06F 3/014 345/418 |
| 6,636,826 | B1* | 10/2003 | Abe | G01C 19/56 702/151 |
| 6,744,420 | B2* | 6/2004 | Mohri | G06F 3/014 345/157 |
| 7,593,757 | B2* | 9/2009 | Yamasaki | G02B 27/017 455/550.1 |
| 7,747,040 | B2* | 6/2010 | Toyama | G06K 9/00228 382/103 |
| 8,310,368 | B2* | 11/2012 | Hoover | A61B 5/1123 340/573.1 |
| 8,451,221 | B2* | 5/2013 | Hwang | G06F 3/0346 345/157 |
| 8,743,052 | B1* | 6/2014 | Keller | G06F 3/014 345/156 |
| 9,020,643 | B2* | 4/2015 | Shimizu | B25J 9/1664 700/245 |
| 9,104,271 | B1 | 8/2015 | Adams | |
| 9,146,618 | B2* | 9/2015 | Tait | G06F 3/017 |
| 9,323,340 | B2* | 4/2016 | Pantel | G06F 3/017 |
| 9,563,528 | B2* | 2/2017 | Ahn | G06F 11/30 |
| 9,685,097 | B2* | 6/2017 | Hoover | G06K 9/00355 |
| 10,137,363 | B2* | 11/2018 | Parshionikar | G06K 9/0053 |
| 2002/0012014 | A1* | 1/2002 | Mohri | G06F 3/014 715/863 |
| 2004/0193413 | A1* | 9/2004 | Wilson | G06F 3/017 704/243 |
| 2006/0019614 | A1* | 1/2006 | Yamasaki | G02B 27/017 455/90.2 |
| 2009/0135009 | A1* | 5/2009 | Little | G06Q 10/00 340/540 |
| 2009/0265470 | A1* | 10/2009 | Shen | G06F 1/1694 709/227 |
| 2009/0303204 | A1* | 12/2009 | Nasiri | A63F 13/06 345/184 |
| 2010/0013860 | A1* | 1/2010 | Mandella | G01B 21/04 345/650 |
| 2010/0149095 | A1* | 6/2010 | Hwang | G06F 3/0346 345/157 |
| 2010/0267424 | A1 | 10/2010 | Kim | |
| 2011/0129124 | A1* | 6/2011 | Givon | G06F 3/011 382/107 |
| 2011/0267456 | A1* | 11/2011 | Adermann | H04N 7/181 348/135 |
| 2011/0317871 | A1 | 12/2011 | Tossell et al. | |
| 2012/0056846 | A1* | 3/2012 | Zaliva | G06F 3/0416 345/174 |
| 2012/0075196 | A1 | 3/2012 | Ashbrook | |
| 2012/0319940 | A1 | 12/2012 | Bress et al. | |
| 2013/0080811 | A1 | 3/2013 | Low | |
| 2013/0278501 | A1* | 10/2013 | Bulzacki | G06F 3/017 345/157 |
| 2013/0285969 | A1 | 10/2013 | Raffa | |
| 2013/0290911 | A1 | 10/2013 | Prahul et al. | |
| 2014/0002338 | A1* | 1/2014 | Raffa | G06F 1/1694 345/156 |
| 2014/0023984 | A1* | 1/2014 | Weatherly | A61B 1/00016 433/31 |
| 2014/0098018 | A1* | 4/2014 | Kim | G06F 3/014 345/156 |
| 2014/0282275 | A1 | 9/2014 | Everitt et al. | |
| 2014/0320434 | A1* | 10/2014 | Pantel | G06F 3/017 345/173 |
| 2014/0363076 | A1* | 12/2014 | Han | G06K 9/6259 382/159 |
| 2014/0368428 | A1* | 12/2014 | Pinault | A63F 13/06 345/156 |
| 2015/0047017 | A1 | 2/2015 | Kim | |
| 2015/0077336 | A1 | 3/2015 | Elangovan | |
| 2015/0138075 | A1* | 5/2015 | Nakasu | G06F 3/017 345/156 |
| 2015/0205566 | A1* | 7/2015 | Osterhout | G06F 3/038 345/156 |
| 2015/0242002 | A1 | 8/2015 | Altman et al. | |
| 2016/0015280 | A1* | 1/2016 | Hyde | G16H 50/30 600/301 |
| 2016/0026212 | A1* | 1/2016 | Lee | G06F 1/163 361/679.03 |
| 2017/0010677 | A1* | 1/2017 | Roh | G06F 3/0488 |
| 2018/0364810 | A1* | 12/2018 | Parshionikar | G06F 3/0346 |

OTHER PUBLICATIONS

Notice of Allowance received in corresponding U.S. Appl. No. 14/591,878, dated Feb. 14, 2019, pp. 1-11.

* cited by examiner

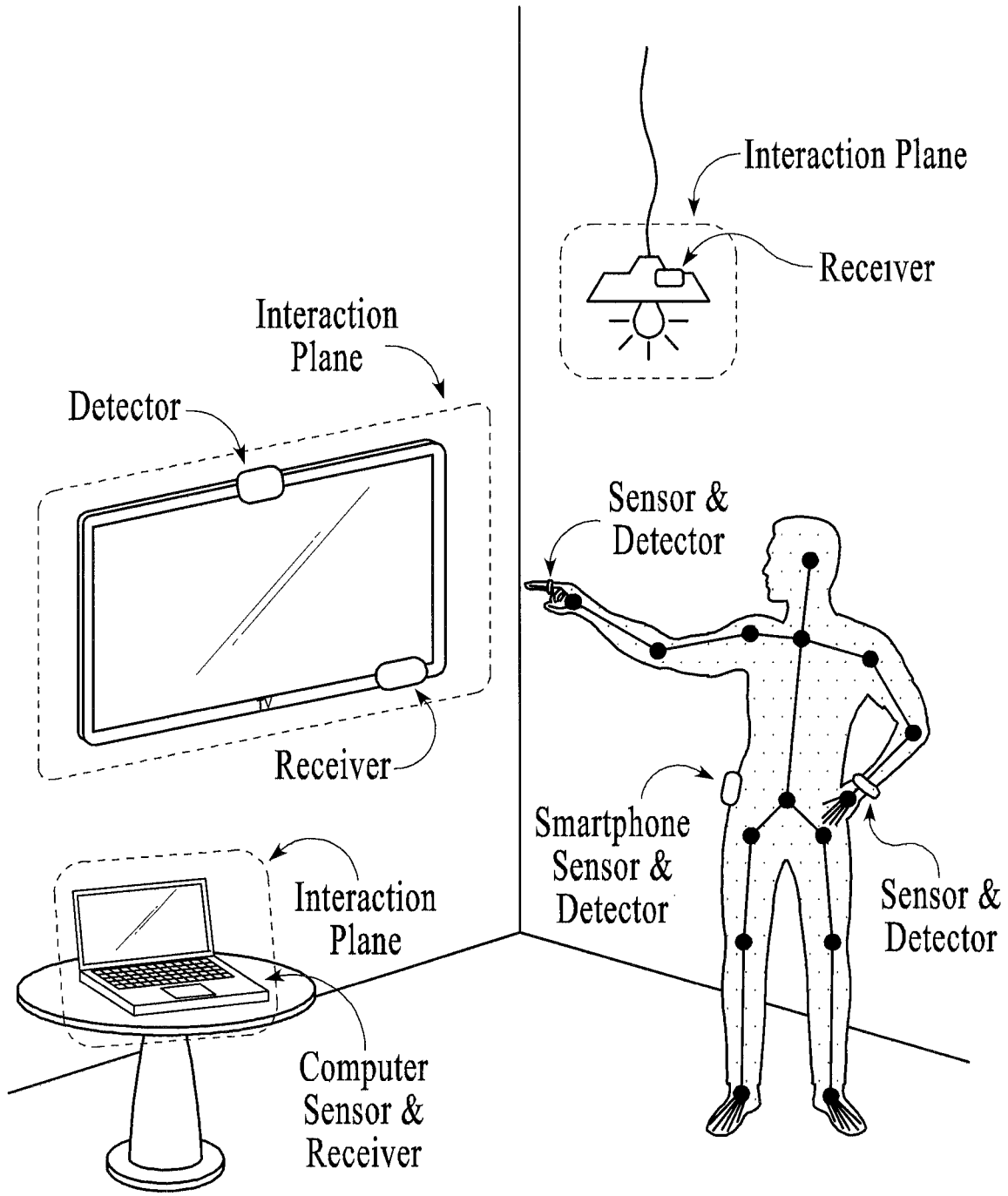
FIG. 1B/1

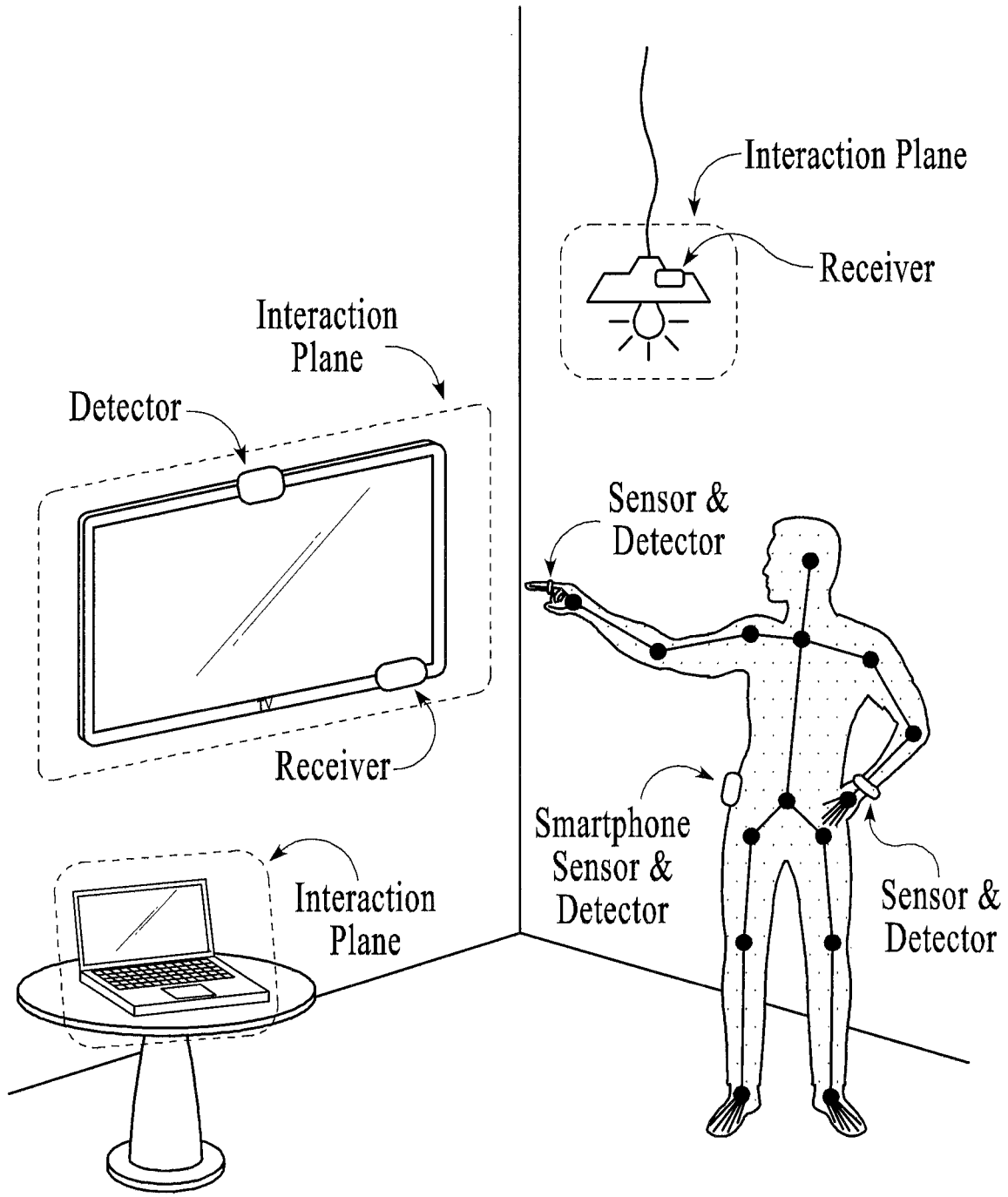
FIG. 1B/2

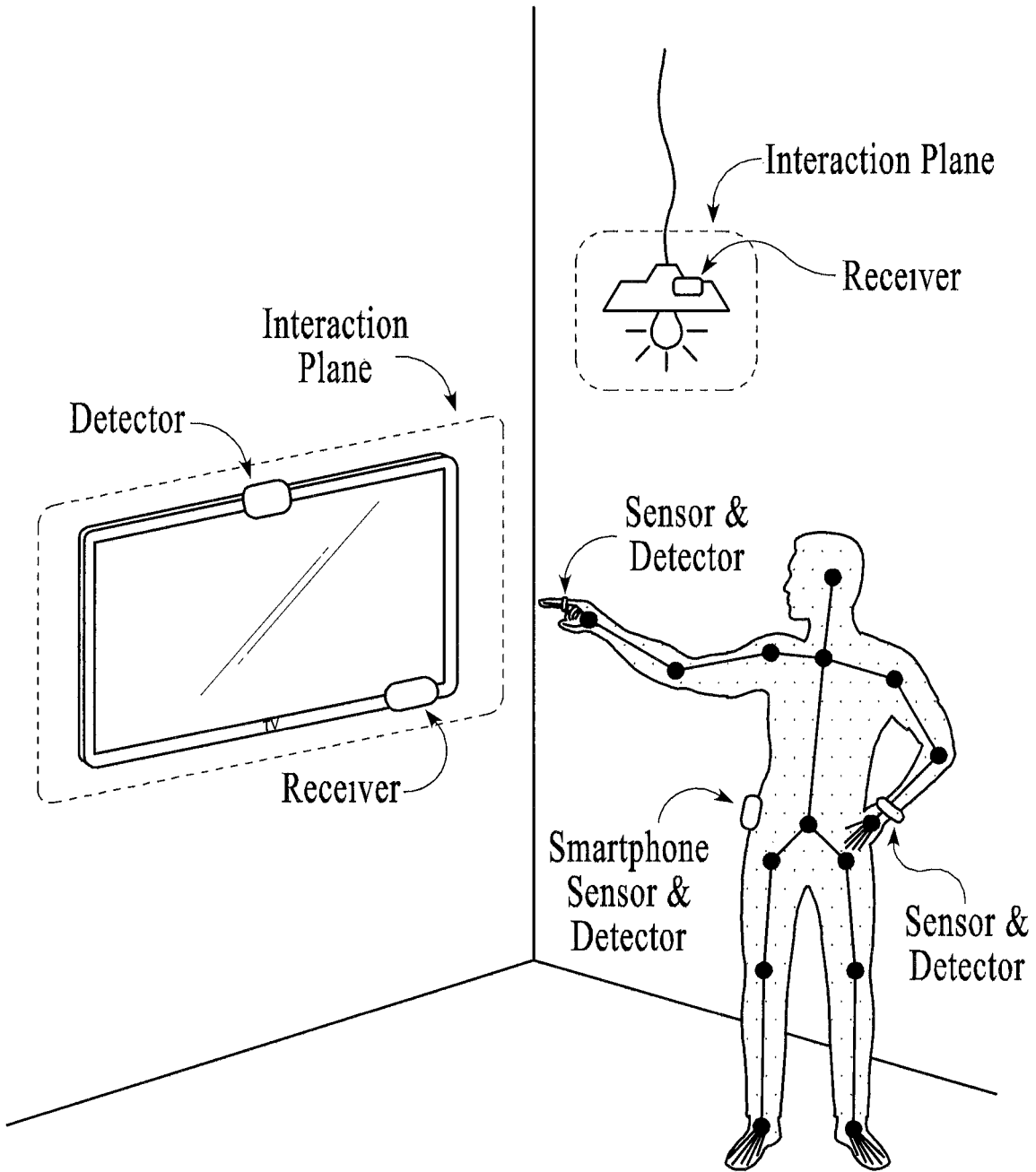
FIG. 1B/3

METHODS AND APPARATUS FOR RECOGNITION OF A PLURALITY OF GESTURES USING ROLL PITCH YAW DATA

RELATED APPLICATION

This application is a continuation in part of U.S. application Ser. No. 14/591,878 filed Jan. 7, 2015 and entitled "Methods And Apparatus For Recognition Of Start And/Or Stop Portions Of A Gesture Using An Auxiliary Sensor," that claims priority to U.S. Provisional Patent Application Ser. No. 61/924,682 filed Jan. 7, 2014, each of which are incorporated by reference herein.

FIELD OF THE ART

This disclosure relates to using the Human body as an Input mechanism, and, in particular, recognition of a plurality of gestures using roll pitch and yaw data, typically in combination with start and/or stop portions of a gesture using an auxiliary sensor.

BACKGROUND

Many conventional gestural systems attempt to detect gestures that resemble characters or words. Such conventional gestural systems, however, offer very poor recognition rates.

SUMMARY

Described are apparatus and methods for reconstructing a plurality of gestures using roll pitch and yaw data, typically in combination with data for recognition of start and/or stop portions of the gesture using an auxiliary sensor, such as a capacitive touch sensor or a MEMS sensor.

BRIEF DESCRIPTION OF THE DRAWINGS

FIG. 1(B)1 illustrates a system diagram according to an embodiment.

FIG. 1(B)2 illustrates a system diagram according to another embodiments.

FIG. 1(B)3 illustrates system diagram according to a further embodiment.

FIG. 2 illustrates that the system allows for the sensor 3 to be used for one gesture one pointing to a light (1) as shown in FIG. 2, and another gesture when pointing at the computer (2) as shown.

FIGS. 3, 4, and 5 show embodiments for micro-gesture recognition according to the embodiments.

DETAILED DESCRIPTION OF THE PREFERRED EMBODIMENT

Figure 1A:
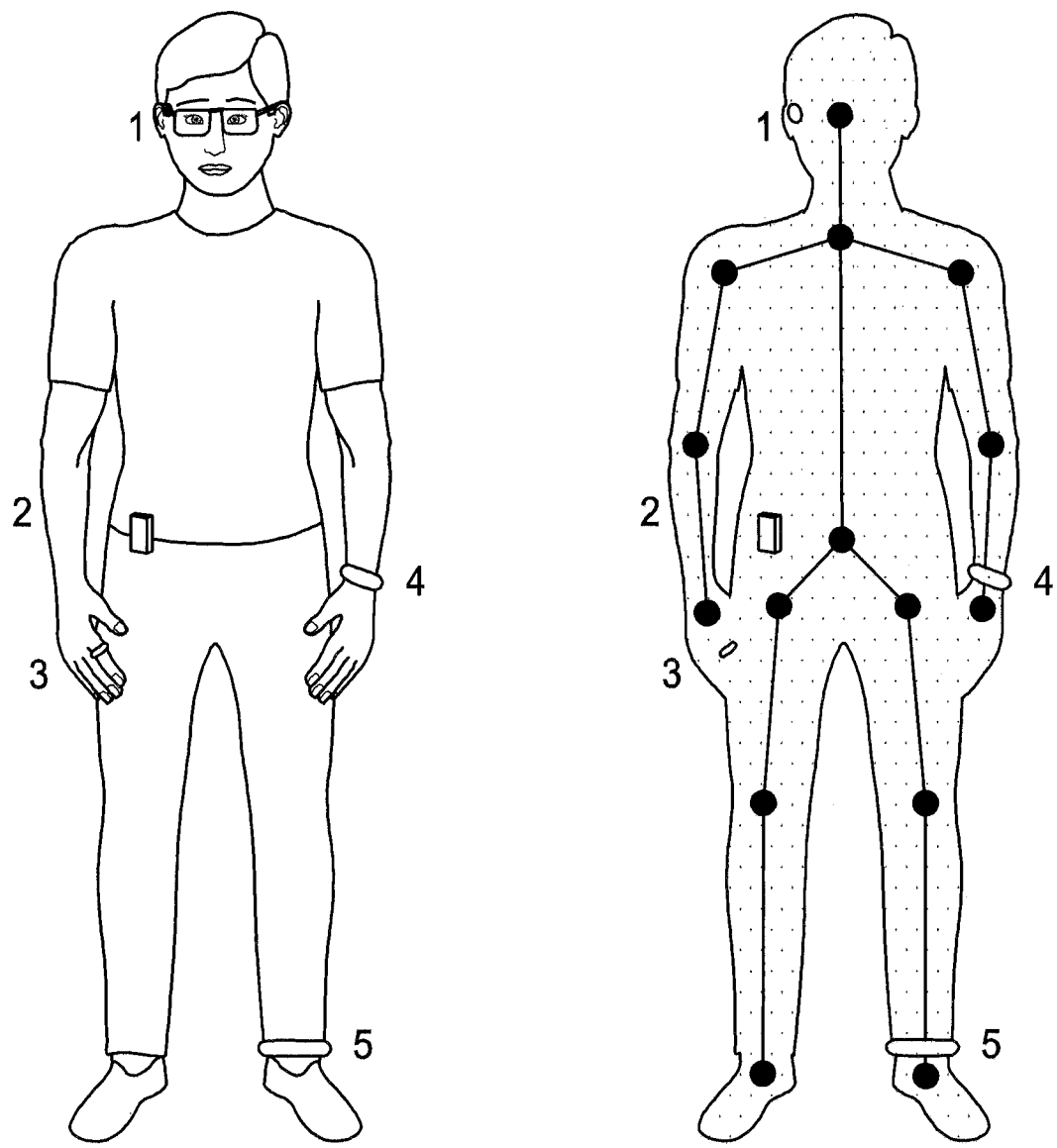
FIG. 1(A) illustrates the skeletal rendering of the human with various nodes, and the usage of many different sensors according to the embodiments.

Various devices such as computers, televisions, electronic devices and portable handheld devices can be controlled by input devices such as a computer mouse or keyboard. Various sensors such as accelerometers, gyroscopes, compasses and cameras can be collectively used (all from a substantially single point such as if disposed on a single ring; or from multiple different locations) to estimate and/or derive a gesture that is intended to have some significant meaning. These sensors dynamically provide data for varying periods of time when located in the associated space for sensing, and preferably stop or go into a low power mode when not in the associated space. When sensor data is unavailable, various calculations may be employed to reconstruct the skeletal structure without all the sensor data.

Various poses and gestures of the human skeleton over a period of time can be aggregated to derive information that is interpreted (either at the sensor or at the device) and communicated over wireless channels such as WiFi, Bluetooth or Infrared to control various devices such as computers, televisions, portable devices and other electronic devices, as described further herein and in the previously filed U.S. patent application Ser. No. 14/487,039 filed Sep. 14, 2014, which claims priority to U.S. Provisional Patent Application 61/877,933 filed Sep. 13, 2013, and entitled "Methods and Apparatus for using the Human Body as an Input Device", which are explicitly incorporated herein by reference.

Described are apparatus and methods for reconstructing a gesture by aggregating various data from various sensors, including data for recognition of start and/or stop portions of the gesture using an auxiliary sensor, such as a capacitive touch sensor or a MEMS sensor.

In a preferred embodiment, MEMS sensors, and preferably a plurality of them within a substantially single location such as on a ring, or in a head mounted device, or in a capsule either directly mounted on the body or enclosed in a garment or clothing, or some other wearable form factor are used, in combination with a capacitive touch sensor or a tactile switch or sensors used for recognition of start and/or stop portions of the gesture. MEMS sensors provide the advantage of not requiring a separate detector compared to conventional camera based depth sensors and don't have to be in the very restricted viewing area of a conventional depth camera. A plurality of MEMS sensors can be used to obtain further information than would be possible with a single such sensor, as described herein. When further used in combination with accelerometers, gyroscopes, compasses, the data from the various sensors can be fused and interpreted to allow for sensing of micro-gestures, as described herein.

Such a single sensing device having multiple sensors can be integrated into everyday objects such as clothing, jewelry and wearable devices like fitness monitors, virtual reality headsets, or augmented reality glasses in order to use of the human body as a real-time input device that can interact with a machine in its surroundings.

Processing of all the data generated to accurately detect the pose of the human body in real-time includes engineering desiderata of event stream interpretation and device power management, as well as usage of algorithms such as Kalman filtering, complementary filters and other conventional algorithms used to fuse the sensor data into coherent pose estimates. The filtering algorithms used are based on the locality of the sensor and factor in the human anatomy and the joint angles of the bones the sensors are tracking. The fused data is then processed to extract micro-gestures—small movements in the human body which could signal an intent, as described herein.

Gestures such as waving your arm from one side to another or micro-gestures such as swiping your index finger from one side to another are mapped to functions, such as changing channels on a TV or advancing the song being played. More complex gestures, such as interacting with the User Interface of a tablet computer are also possible using micro-gestural primitives to generate a more complex macro intent that machines in the environment can understand. All of these gestures, however, must have start points and stop points, which need to be detected in some manner.

Thus an aspect of the system includes assembling a movement sequence (aka gesture) that could be used to indicate a command, for example, which has a start point and a stop point. Each gesture can also take on a different meaning depending on which device it is communicating with. Thus, pointing to a Television and moving your hand from one direction to another can imply changing the channel while a similar such gesture could imply changing the light intensity when done pointing to a light bulb, with each of the Television and the light bulb being separate subspaces that are detected as such by an overall detector, for example.

Efficient power management strategy is also provided, such that the sensor device doesn't require a power on or power off switch. This involves determining the current state of gestural detection and further includes the ability to turn off components such as the gestural detection unit, or various sensors to save power, and in particular using a capacitive touch sensor or a tactile switch or a specific gesture or any combination of the three as described hereinafter to accomplish certain of these power savings.

It is noted that the single sensing device is a battery-operated device, yet it does not necessarily have a power button. It does, however, have capacitive touchpads and tactile switches as described, which can be programmed to activate and/or de-activate the single sensing device, thereby ensuring that the device is in use only when the user intends for it to be and keeping it energy-efficient.

As described further herein, an auxiliary sensor, such as a capacitive touchpad or a tactile switch on the wearable input platform, also referred to as single sensing device or ring herein, upon receiving a specific input (i.e. tactile, capacitive touch, gesture or combination thereof) from the user, enables the communication and connectivity channels on the platform and signals to the gesture acquisition engine to start acquiring gesture data and manipulating such gesture data to interact with a specific application device. Similarly, the same or different touch input, when applied to the touchpad, can disable (or send into an idle state) the communication and connectivity channels on the platform to signify an end to the interaction with the device, thereby stopping the gesture acquisition engine from continuing to acquire data.

This capacitive touch sensor and tactile switch feature takes the uncertainty out of the gesture acquisition engine, whereby it is not trying to interpret a random gesture, unless expressly instructed to do so, via the touch input imparted to the capacitive touchpad or tactile button. Additionally, the capacitive touch sensor feature ensures that the single sensing device is energy efficient and active only as needed for the duration of the interaction. Similarly, the gesture acquisition engine is not "always-on" and in use only when needed, thereby conserving energy.

The specific input imparted to the touchpad can vary, depending on additional touch gestures that could be programmed, depending on the use case. If the wearable input platform is purely intended for gesture control, then any kind of input would suffice for the purpose of starting and stopping the gesture acquisition. However, there may be instances, where the wearable input platform could be used to control a music player on a smartphone or some similar device, thereby requiring more than one type of input. In such an instance, a long contact with the touchpad could signal the start of the device control using the input platform. Further, a short contact with the touchpad could indicate pausing the track, a swipe to the left could mean going to the previous track, etc. The preceding touch inputs are meant to be an example of what is possible for a given use case. Hence, in such a scenario, it is important that the start/stop gesture detection inputs are sufficiently distinguished from other device operation touch inputs.

Figure 2:
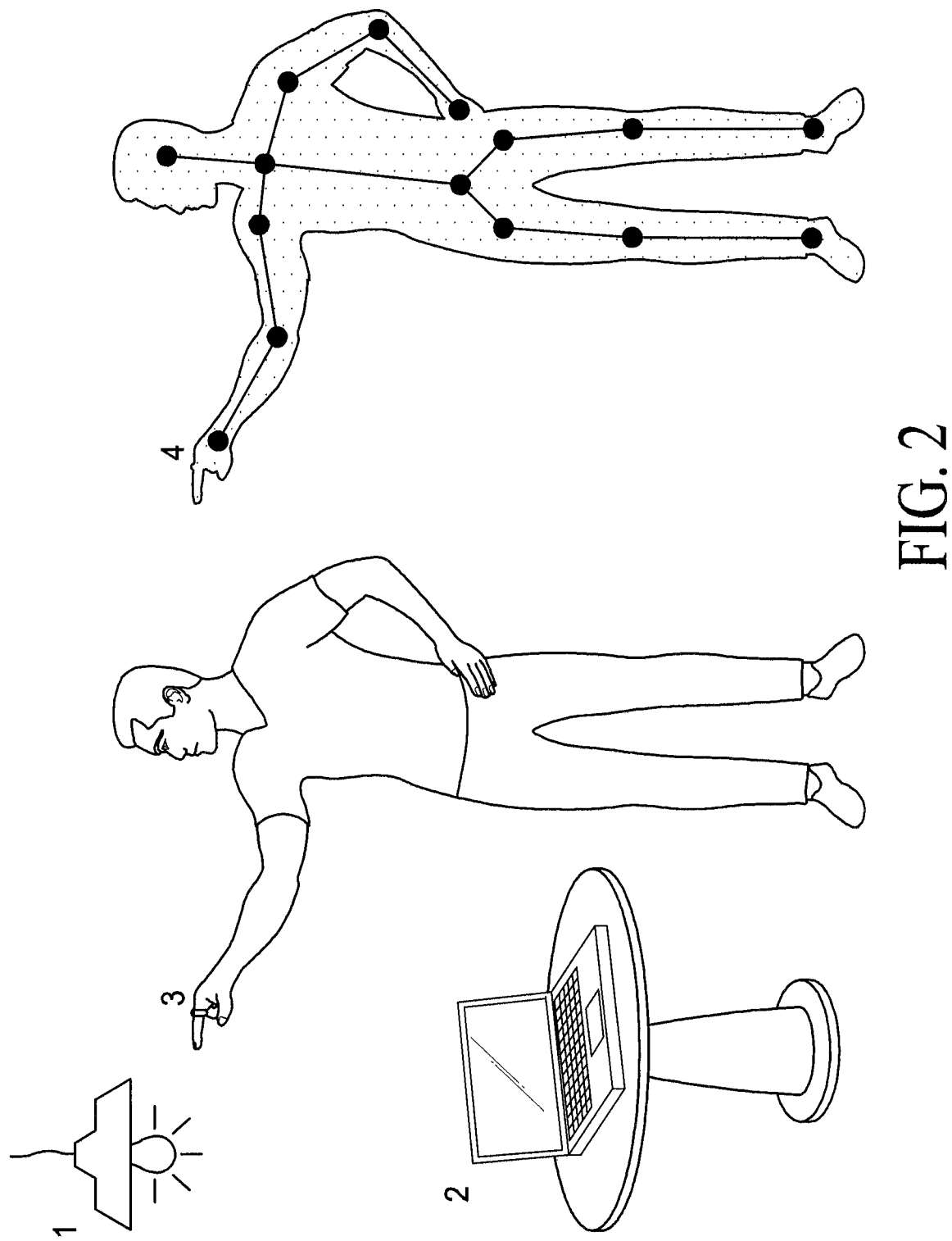
Figure 3:
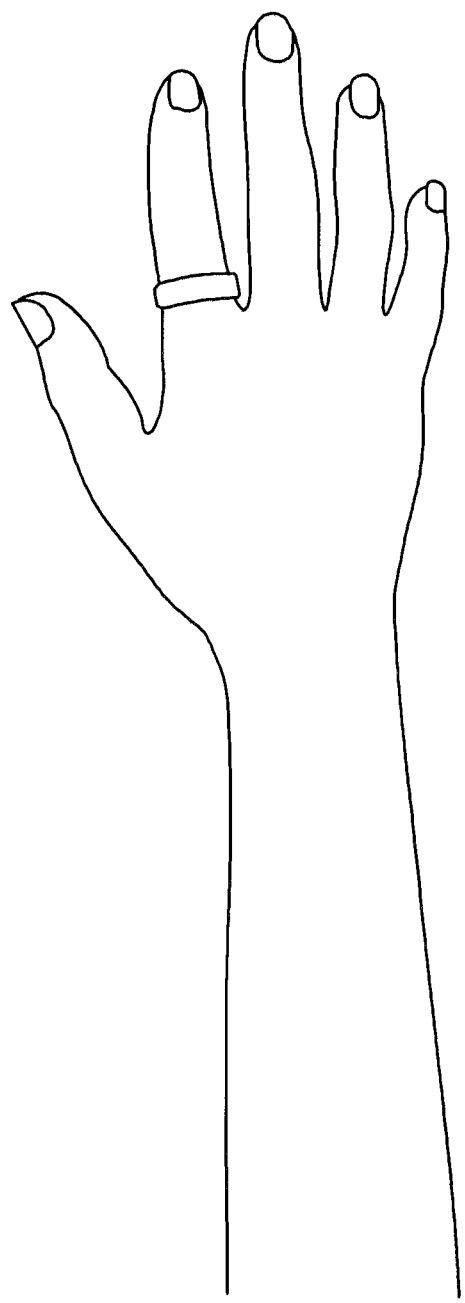

These various aspects are shown in the diagrams attached. FIG. 1(A) illustrates the skeletal rendering of the human with various nodes, and the usage of many different sensors: one on the glasses (1), another on the belt (2), a third of a number of different sensors for fingers (3), one for the wrist (4) and one on an ankle bracelet or attached to the bottom of the pants worn (5). FIG. 1(B)(1-3) shows a similar space and rendering, and points out specific sub-spaces associated with different objects; each of which can have their own relative coordinate system if needed. As shown, FIG. 1(B)1 illustrates a system diagram with a laptop as a third controllable device, which laptop includes an interaction plane and is labeled as Computer Sensor & Receiver to illustrate that it can operate the software needed to fuse different sensor data together, as described elsewhere herein. FIG. 1(B)2 illustrates a system diagram with a laptop as well, but this laptop shown only as having an interaction plane, and operate upon a distributed system (such as with cloud processing). FIG. 1(B)3 illustrates an even simpler, which does not include the laptop at all within it. As is apparent, many different combinations are possible and within the contemplated scope herein.

As described above, the system allows for the sensor 3 to be used for one gesture one pointing to a light (1) as shown in FIG. 2, and another gesture when pointing at the computer (2) as shown.

Figure 4:
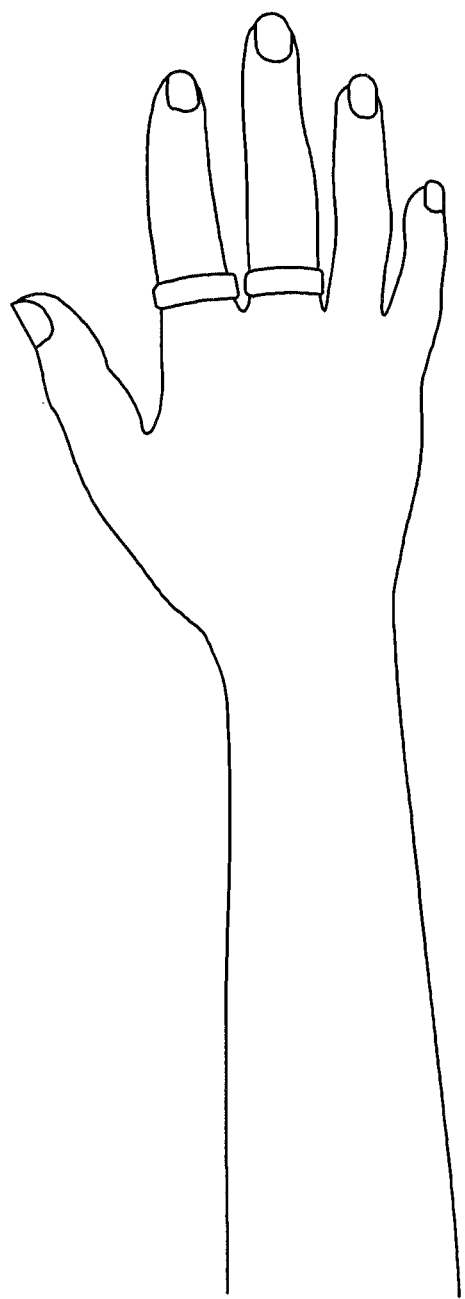
Figure 5:
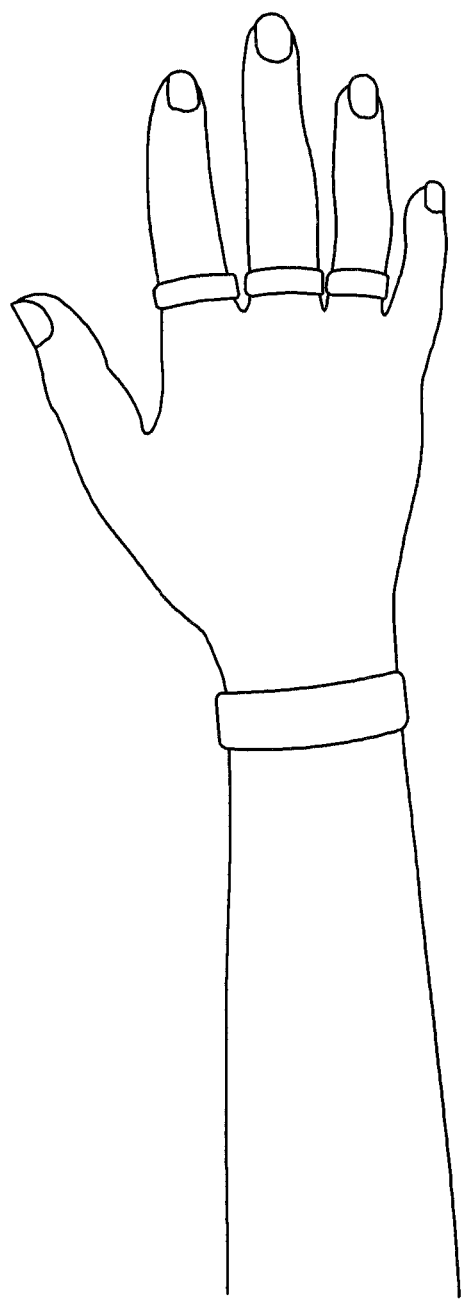

FIGS. 3, 4, and 5 show embodiments for micro-gesture recognition that include usage of 1, 2 and 3 finger rings, respectively, as shown. Other configurations are possible and within the intended scope herein.

Figure 6:
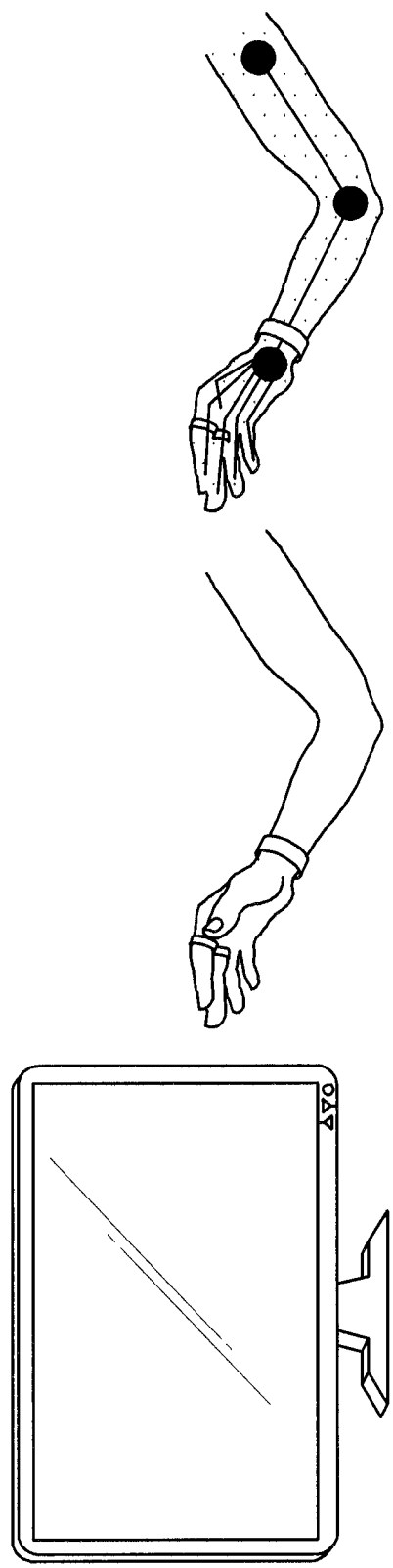
FIG. 6 shows an illustration of micro-gestures detected within a subspace that has its own relative coordinate system.

FIG. 6 shows an illustration of micro-gestures that are detected within a subspace around a computer, which subspace can have its own relative coordinate system, rather than being based upon absolute coordinates. In addition to the MEMS sensor data in each ring, radio strength can also be used to detect distance from a relative reference point, such as the screen of the computer. Additionally, the relative coordinate system can be based on the part of the body to which the single sensing device is attached, with a ring on a finger having as a relative coordinate system the portion of the arm from the elbow to the wrist as one axis.

Figure 7:
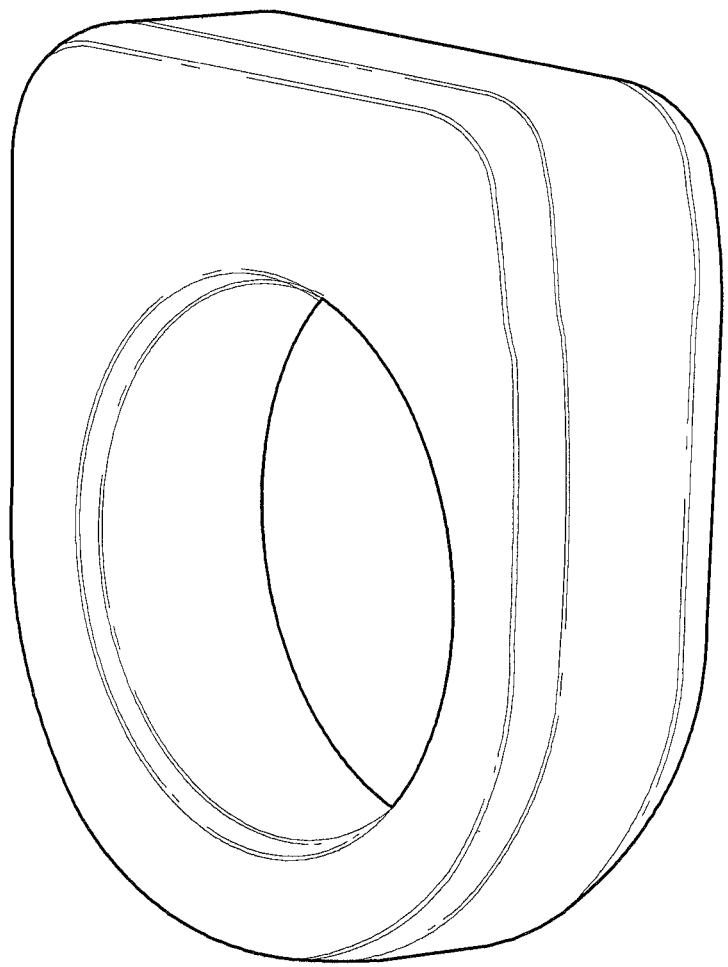
FIG. 7 illustrates a 3D exterior view of a single ring sensor.
Figure 8:
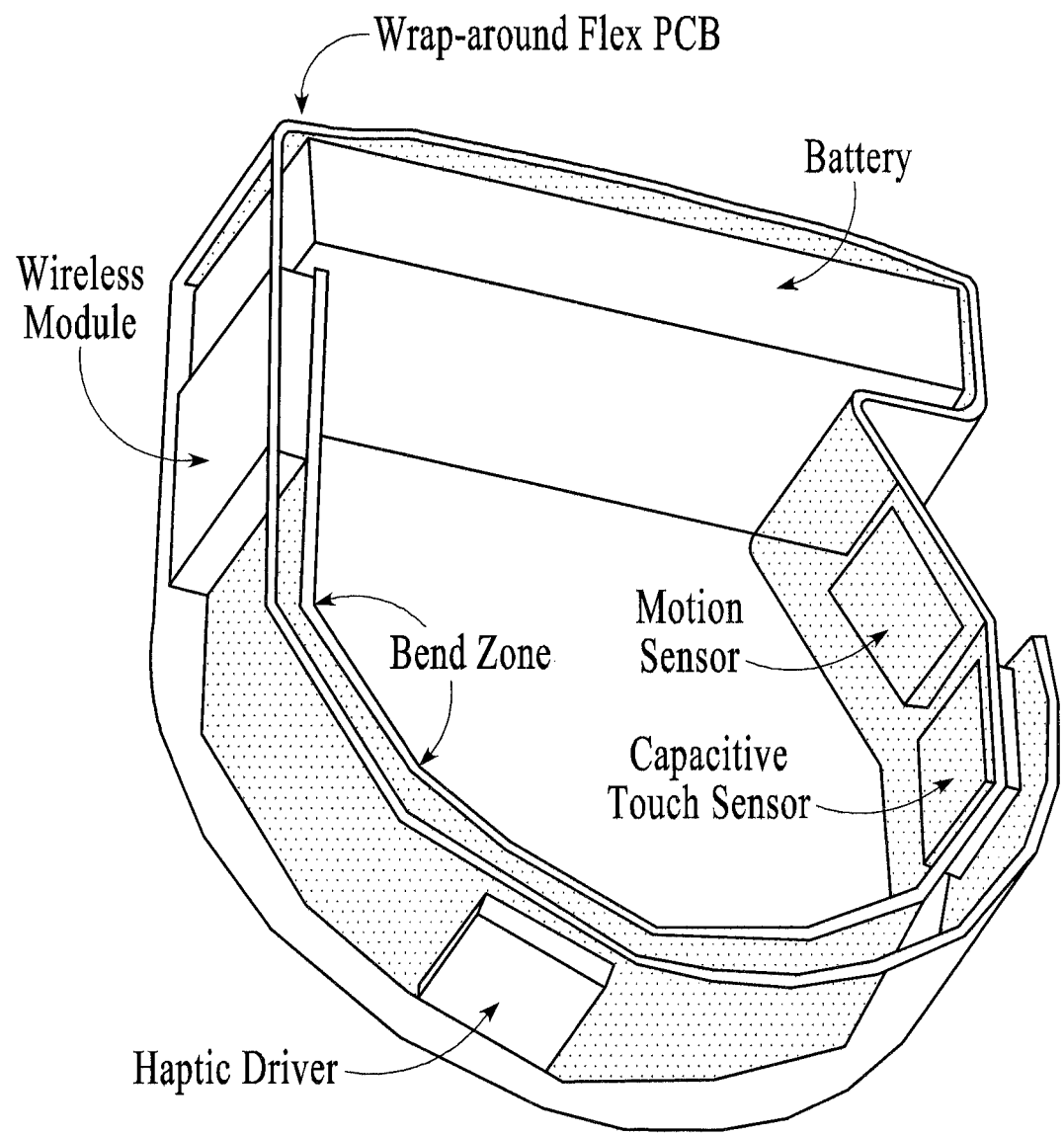
FIG. 8 illustrates a more detailed view of the ring sensor of FIG. 7.
Figure 9:
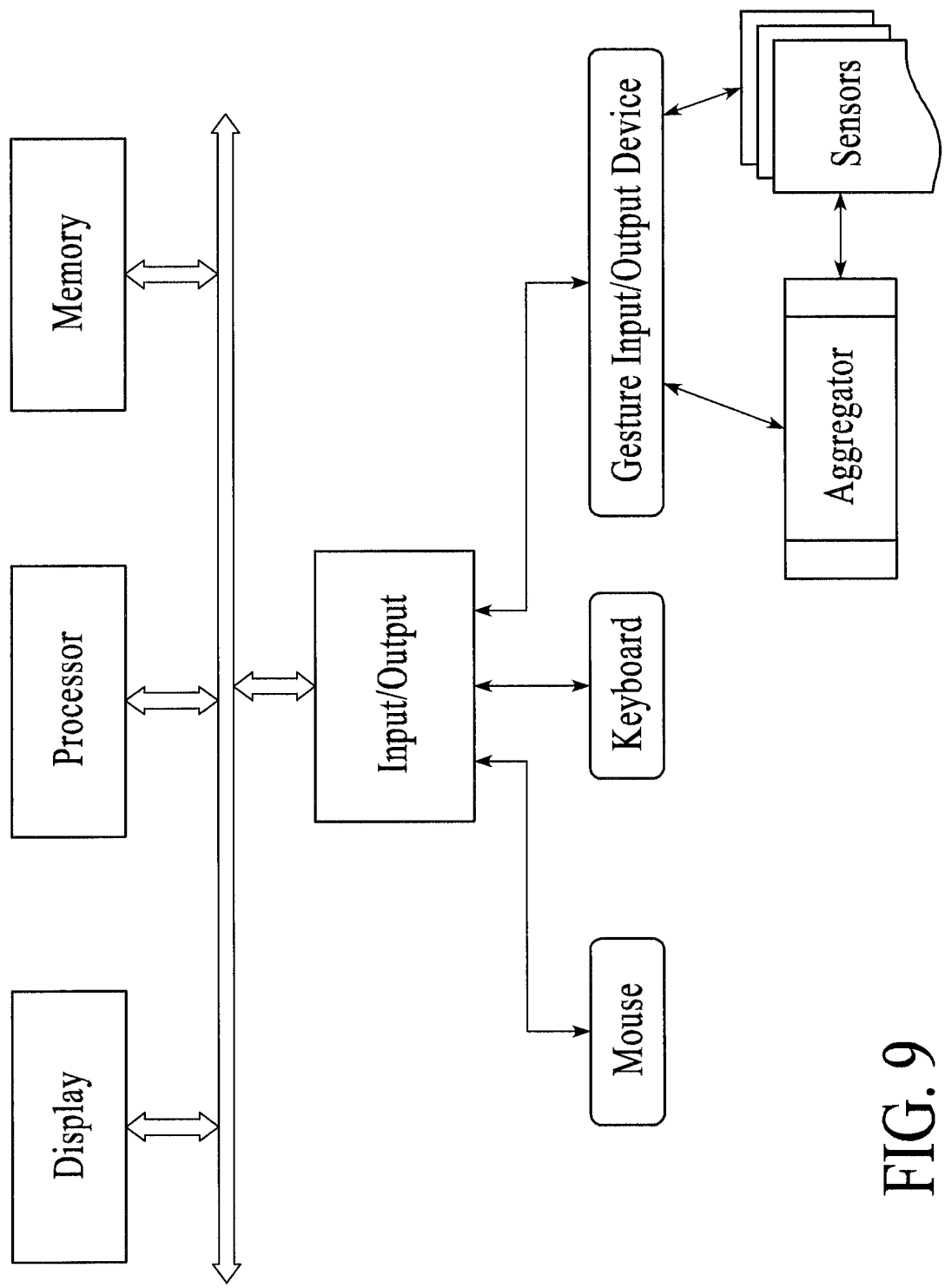
FIG. 9 illustrates a computer sensor & receiver according to the embodiments.

FIG. 7 illustrates a 3D exterior view of a single ring sensor, and FIG. 8 illustrates that ring sensor in a more detailed view, with the significant electronic components identified, and which are connected together electrically as a system using a processor, memory, software as described herein, including other conventional components, for controlling the same. The processor controls the different sensors on the ring device and is in charge of detecting activity in the various sensors, fusing the data in them and sending such data (preferably fused, but in other embodiments not) to other aggregators for further processing. While shown as a ring sensor, this combination of elements can also be used for the other sensors shown in FIG. 1—though other combinations can also be used. Note that while only a single capacitive touch sensor is shown, that multiple capacitive touch sensors can be included and with tactile switches FIG. 9 illustrates a Computer Sensor & Receiver as shown in FIG. 1(B1). As illustrated in FIG. 9, included are a processor, memory and display that are used as is conventionally known. The processor controls the different sensors on the various devices and can fuse the data from disparate devices that has been aggregated previously or not, and send such data (preferably fused, but in other embodiments not) to other aggregators for further processing as well as send control signals based on the what has been detected to control devices such as the light or television as shown in FIG. 1. I/O devices as known are also included, as well as what is labeled a Gesture Input/Output Device and an Aggregator coupled thereto (which Aggregator may be part of the Computer Sensor and Receiver or could be located elsewhere, such as on a wrist sensor as described above). The Aggregator can be implemented in hardware or software to process the various streams of data being received from the various sensors. The Aggregator factors in location of the sensor (e.g: on the finger or wrist etc.) and calculates what data is relevant from this sensor. This is then passed on to the Gesture Input/Output Device (which could also reside across a wireless link) to control various computing devices.

The device that could be worn on the ring could possess a Capacitive Touch surface or a tactile switch on the exterior of the device (preferably the entire exterior surface or an entire portion of an exterior surface associated with a single Capacitive Touch Sensor or multiple touch-sensitive areas of varying lengths and sizes) and a Capacitive Touch Sensor enclosed in the inside of the device.

The device can also possess a haptic actuator and associated circuitry to be able to provide a haptic feedback based on user engagement with a computing device. The device can also support various forms of wireless networking such as NFC, Bluetooth and/or WiFi to be able to interact with various other devices in its surroundings.

Multiple sensors can interact with each other providing a stream of individually sensed data. For example a sensor worn on the ring can communicate with a wrist worn device or a smartphone in the pocket. This data could then be aggregated on the smartphone or wrist worn device factoring in the human anatomy. This aggregation may factor in range of motion of the human skeletal joints, possible limitations in the speed human bones could move relative to each other, and the like. These factors, when processed along with other factors such as compass readings, accelerometer and gyroscope data, can produce very accurate recognition of gestures that can be used to interact with various computing devices nearby.

Figure 10:
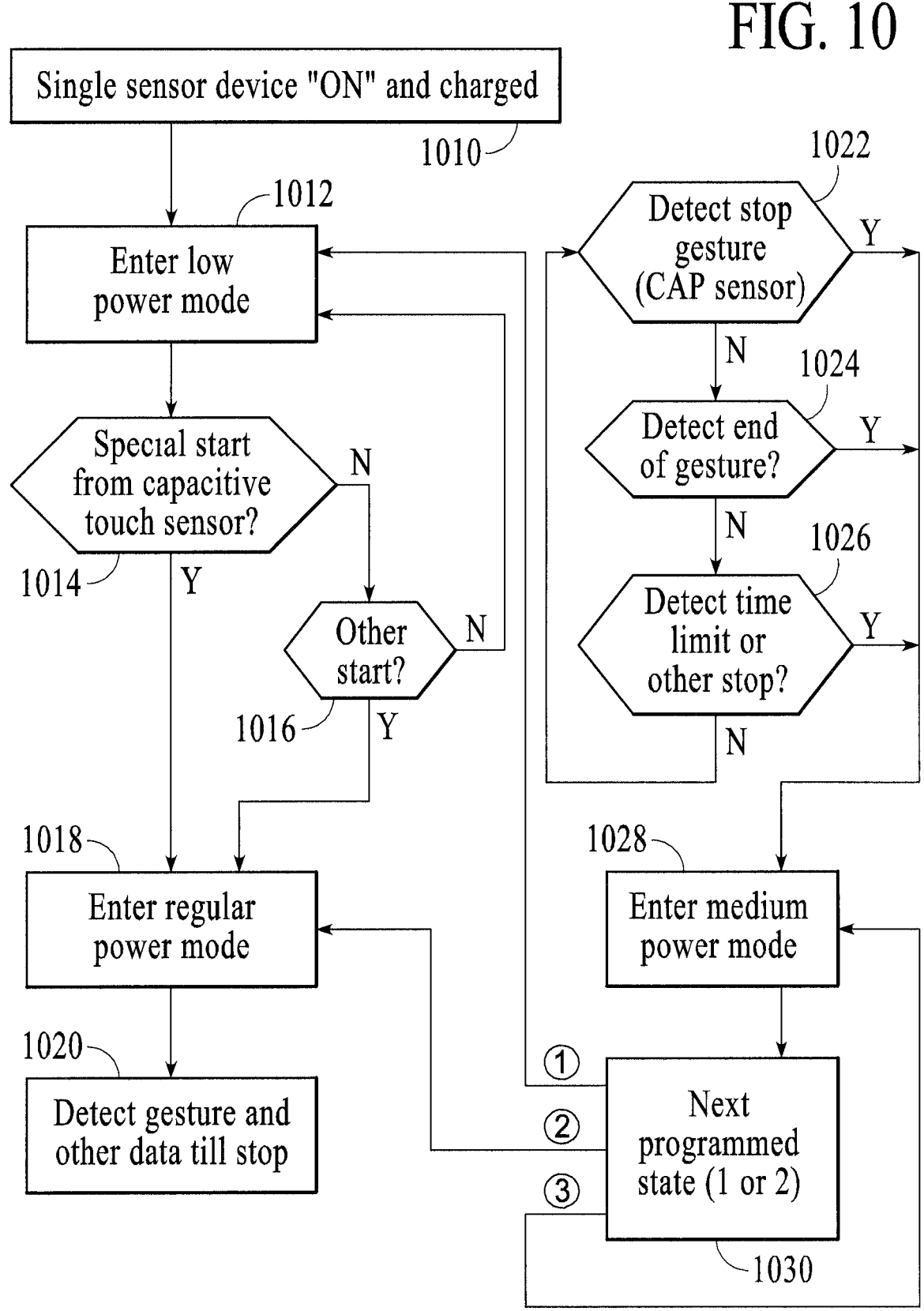
FIG. 10 illustrates a flow chart of operation using the capacitive touch sensor and low power modes.

FIG. 10 illustrates a flowchart of the preferred operation using the capacitive touch sensor and low power modes, which is implemented in application software loaded onto the memory and executed by the processor, in conjunction with the gesture input/output device, aggregator, and sensors. For understanding, operation of a single sensing device is explained, but it will readily be appreciated that the same operations are used for multiple sensing devices, with then one of the sensing devices and/or control devices being the master device.

In operation, step 1010 of FIG. 10 shows the single sensor device being in the "on" state and charged sufficiently for operation. If not charged, then a separate charging station (not shown) can be used to charge the device. After step 1010, step 1012 follows, with entry into a low power mode. In this low power mode, the minimum operations are performed, and as many of the MEMS sensors and the like are put into a sleep state in order to preserve power, with the auxiliary sensor, such as the capacitive touch sensor, being periodically awaken and scanned to see if an event has occurred, in steps 1014. Further, other start events (such as tactile or gestural input) can be programmed, and this is shown as step 1016. In a preferred embodiment, the low power mode has a tactile only input to wake up from deep sleep, and all other sensors are off, as well as wireless transmission/reception. In both the medium and low power modes, wireless transmission/reception is preferably off.

If in either of steps 1014 or 1016 a start signal is detected, then steps 1018 follows, with the single sensor device entering the regular power mode, such that full functionality is possible, though even within full mode power savings procedures can be put in place to conserve power.

One step as shown in the regular power mode is indicated as step 1020 in which gesture and other data are detected, until a stop signal is detected. Other full functionality steps can also occur, such as Processing/transforming the gestures and other sensor data such as acceleration and orientation; transmitting the processed data over a wireless medium to enable interaction with the smart device (TV, smart phone, tablet, etc.)

Steps 1022, 1024 and 1026 all follow, which are each detecting the existence of the end of the gesture. Usage of the capacitive touch sensor to detect a specific stop gesture is shown in step 1022, whereas step 1024 shows that an end of gesture can be detected based upon the gesture data (based on a pre-programmed, unique gesture). Step 1026 indicates that a time limit or other stop trigger (such as a tactile switch) can also be used to generate the stop signal at the end of a gesture.

Upon detection of a stop signal in any of steps 1022, 1024 and 1026, step 1028 follows, and a medium power mode is preferably entered into, in which case the, for example, no further gesture data collection is performed, the MEMS sensors are turned off, and processing of the gesture data collected already is finished using time-keeping, so as to then perform operations in accordance with such processed gesture data. Other functions that may still occur in a medium power mode, that would preferably not occur in a low power mode, are keeping all the sensors sensing (in standby) and waiting for some combination or one of touch/gesture/tactile input for quick startup.

Following step 1028 is a step 1030, in which a preferably programmed determination of whether to then enter into the low power mode 1012, the regular power mode 1018, or stay in the medium power mode 1028.

Figure 11:
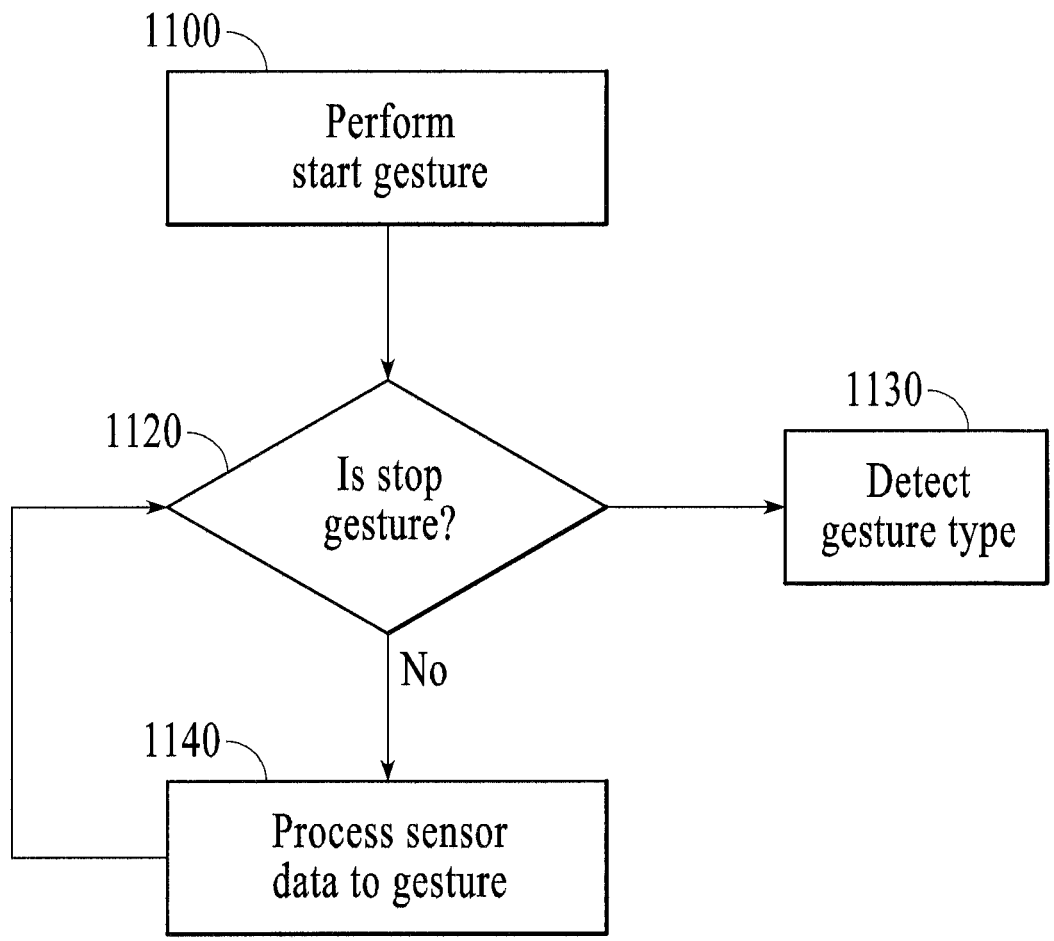
FIG. 11 illustrates a high-level gesture recognition flowchart according to further embodiments.

FIG. 11 illustrates a high-level gesture recognition flowchart according to further embodiments, which are programmed in software, and which automatically run on the processor, of course based upon external inputs as described, which can be manually provided, such as for a start gesture. It is also understood that determination of a gesture, and in preferred embodiments based upon a single sensing device that has multiple sensors integrated therein, is described. As shown, step 1110 indicates that the start gesture, explained previously, has been performed. Step 1120 follows, with a determination of whether a stop gesture has been detected, as explained above. If yes, then step 1130 follows, and the gesture types, explained above and hereinafter, is determined. If no in step 1120, the step 1140 follows, and sensor data for gestures received in the previous period is processed, and then the flow returns to step 1120, as explained above.

Figure 12:
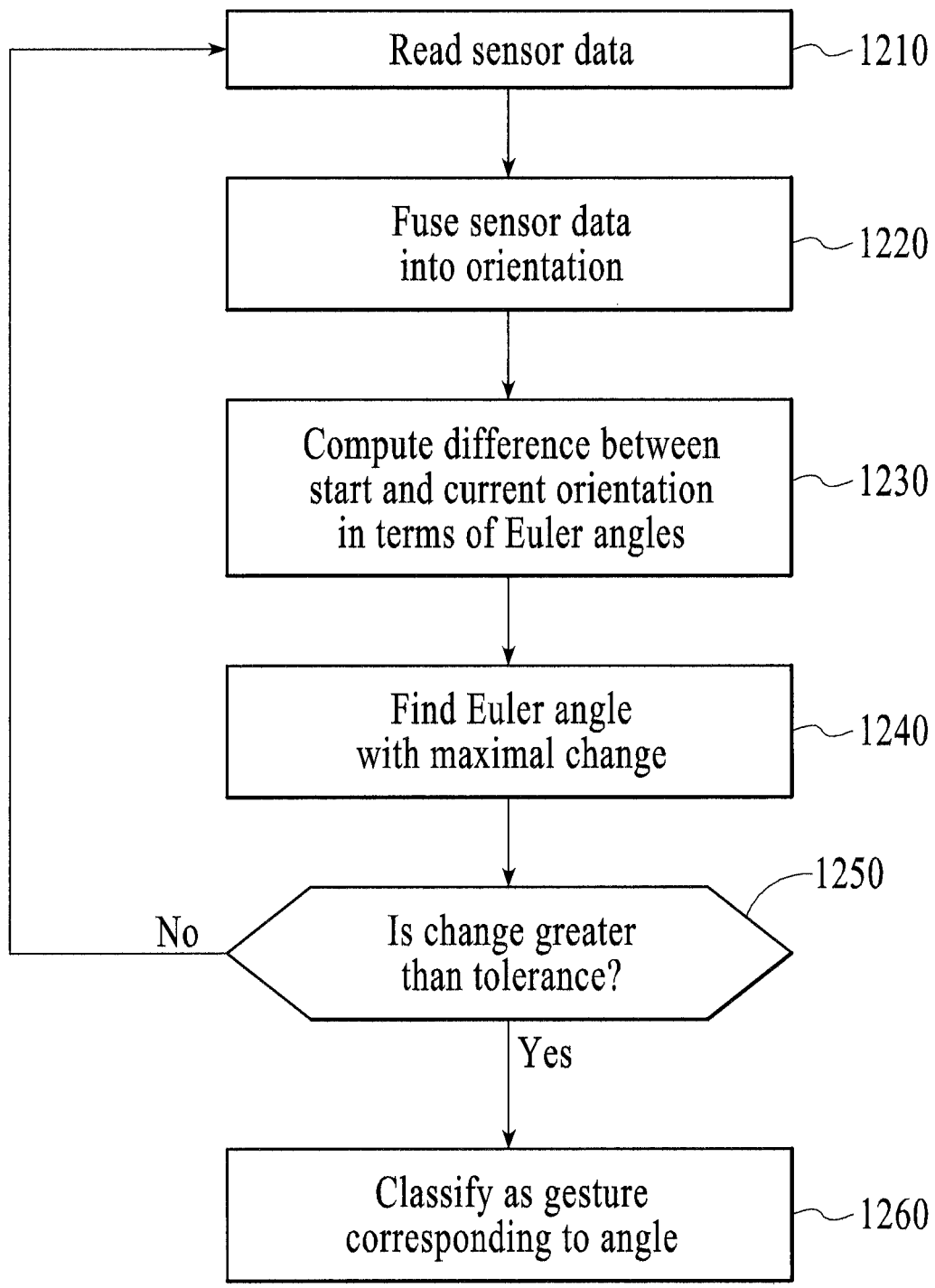
FIG. 12 illustrates a more detailed gesture detection flowchart according to further embodiments.

FIG. 12 illustrates a more detailed gesture detection flowchart according to further embodiments, and particularly the gesture type determination and data processing from steps 1130 and 1140 in FIG. 11 is described in further detail. Sensor data, such as from a start to a time when the sensor data is processed and a stop gesture is then looked for, is read in step 1220. Following step 1220, in step 1220 sensor data is fused to orientation data, which provides the orientation of the single sensing device for which the orientation is desired. Step 1230 then follows, in which the difference between start and current orientation (such as a stop position), in terms of euler angles is determined. In step 120, the euler angle with the maximal change is determined. Thereafter, step 1250 follows, in which the maximal change is compared to a threshold, to see if the change is greater than the threshold (also referred to as tolerance). If no, then further sensor data is read. If the change is greater than the threshold, then step 1260 follows and a gesture is determined, corresponding to the angle.

It will be apparent in the following FIGS. 13, 14 and 15, which correspond to the roll, yaw, and pitch, respectively, that the sequence described above in FIGS. 11 and 12 is used, with modification for each of the roll, yaw and pitch, as described. As such, certain aspects already described will not be repeated.

The below table introduced symbols that are then used in the discussion of following figures.

| Symbol | Units | Description |
| --- | --- | --- |
| $\phi$ | rad | Roll Angle |
| $\theta$ | rad | Angle |
| $\psi$ | rad | Yaw Angle |
| $\epsilon_\phi$ | rad | Roll Angle Tolerance |
| $\epsilon_\theta$ | rad | Pitch Angle Tolerance |
| $\epsilon_\psi$ | rad | Yaw Angle Tolerance |
| $t_\theta$ | sec | Time at start of gesture |
| t | sec | Current Time |
| $|\phi|$ | rad | Absolute value of roll angle |

Figure 13:
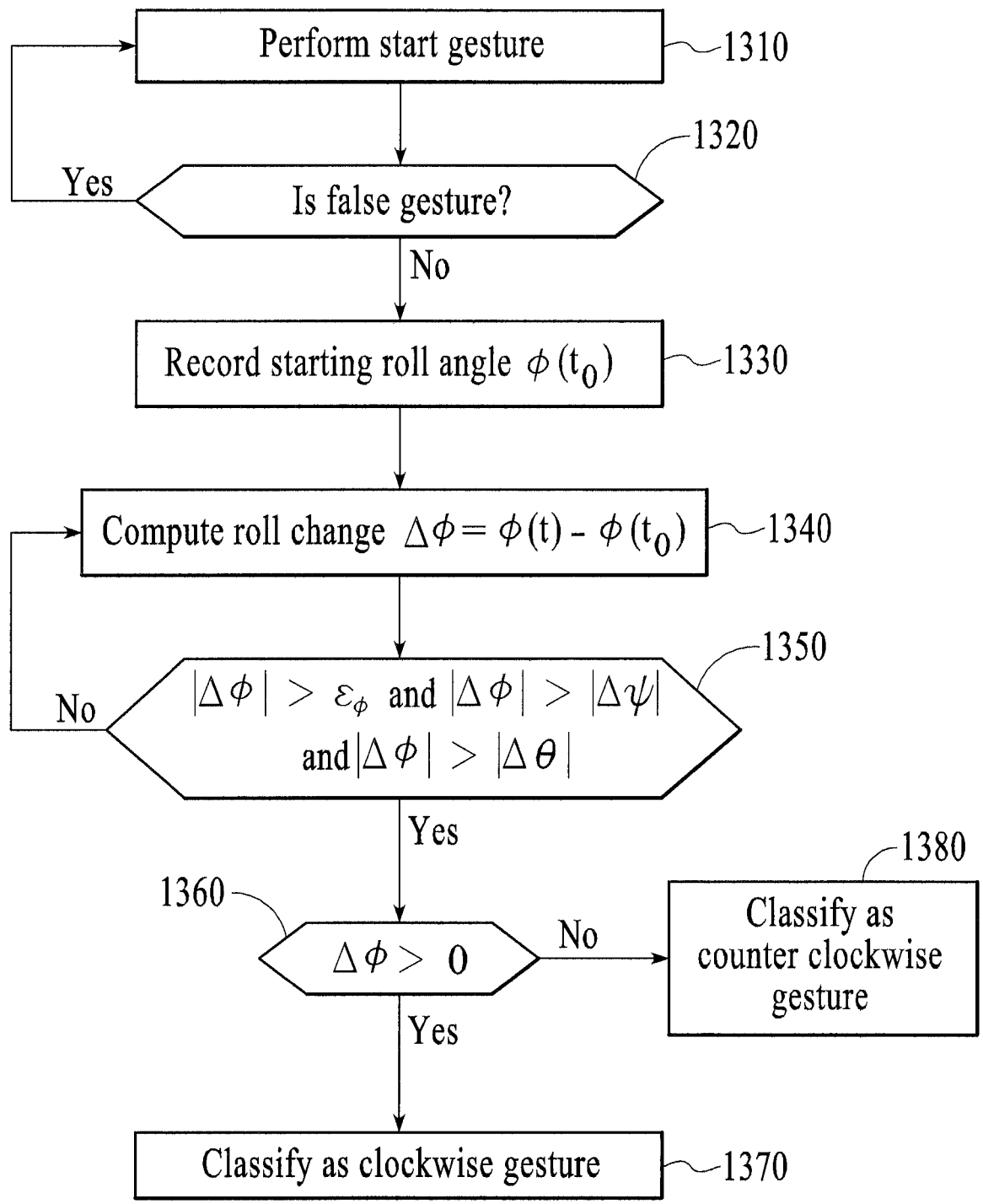
FIG. 13 illustrates a roll gesture detection flowchart according to further embodiments.

FIG. 13 illustrates a roll gesture detection flowchart according to further embodiments. Step 1310 indicates that the start gesture has been performed and detected, as previously described. Step 1320 follows, and a determination of whether the gesture that has been initiated is a true gesture or a false gesture is made. If a false gesture, then a reset is performed, such that determination processor sets another gesture start signal usable as the gesture start signal thereafter, and then the process continues. Assuming the gesture initiated is not a false gesture, then data relating to the roll angle is detected in step 1330. Step 1340 then detects the change in roll angle from the initial position. In step 1350, it is determined that the change in roll angle, in absolute value, is greater than a threshold, and that the change in roll angle is greater than the change in the pitch angle and the change in the yaw angle. If the answer is no, then a return to step 1340 occurs, whereas if the answer is yes, then a determination as to the sign of the change in angle is determined, such that if greater than 0, it is classified as a clockwise gesture in step 1370, and if not greater than 0, then it is classified as a counter clockwise gesture in step 1380.

Figure 14:
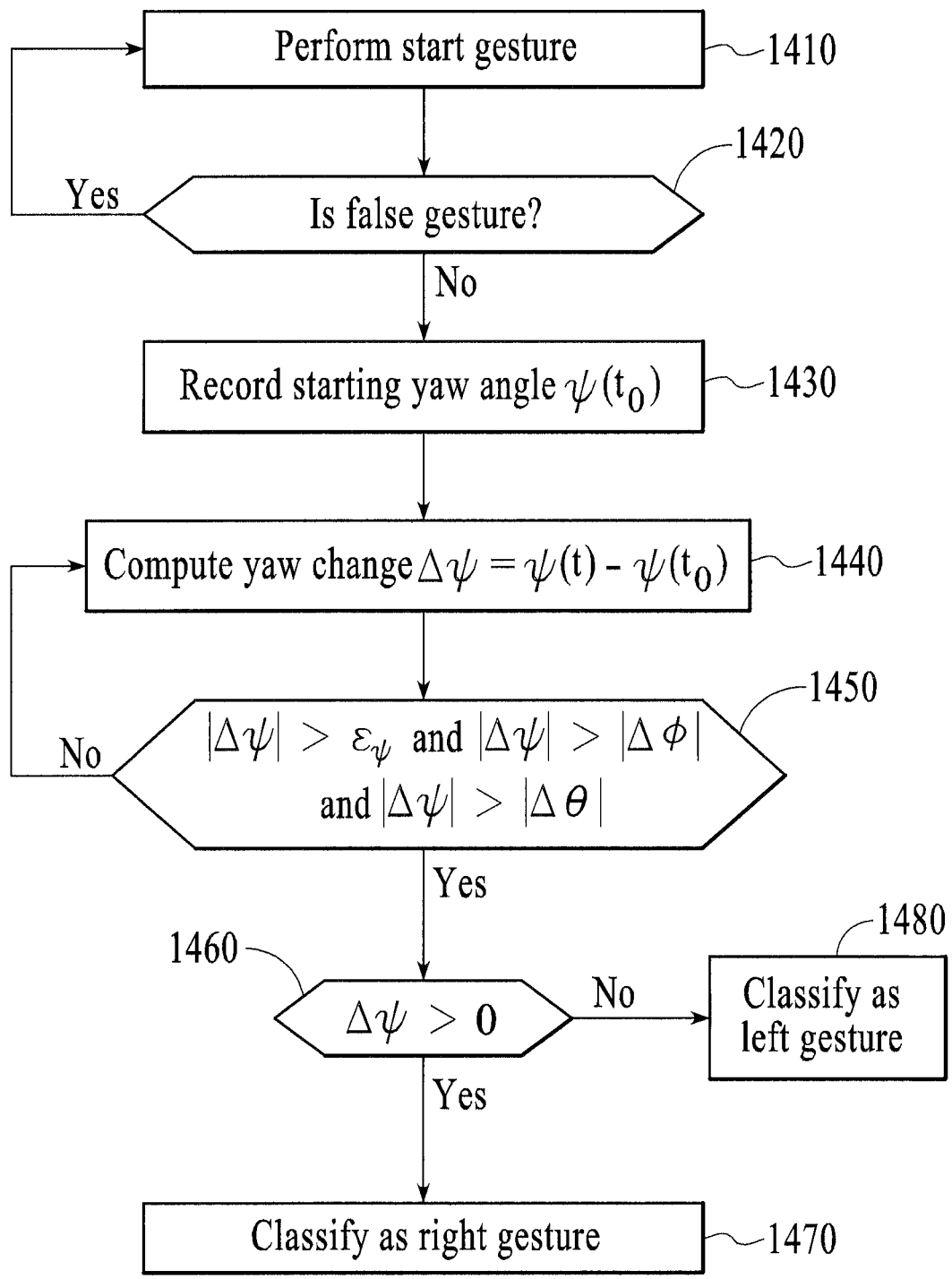
FIG. 14 illustrates a yaw gesture detection flowchart according to further embodiments.

FIG. 14 illustrates a yaw gesture detection flowchart according to further embodiments. Step 1410 indicates that the start gesture has been performed and detected, as previously described. Step 1420 follows, and a determination of whether the gesture that has been initiated is a true gesture or a false gesture is made. If a false gesture, then a reset is performed, such that determination processor sets another gesture start signal usable as the gesture start signal thereafter, and then the process continues. Assuming the gesture initiated is not a false gesture, then data relating to the yaw angle is detected in step 1430. Step 1440 then detects the change in yaw angle from the initial position. In step 1450, it is determined that the change in yaw angle, in absolute value, is greater than a threshold, and that the change in yaw angle is greater than the change in the pitch angle and the change in the roll angle. If the answer is no, then a return to step 1440 occurs, whereas if the answer is yes, then a determination as to the sign of the change in angle is determined, such that if greater than 0, it is classified as a right gesture in step 1470, and if not greater than 0, then it is classified as a left gesture in step 1480.

Figure 15:
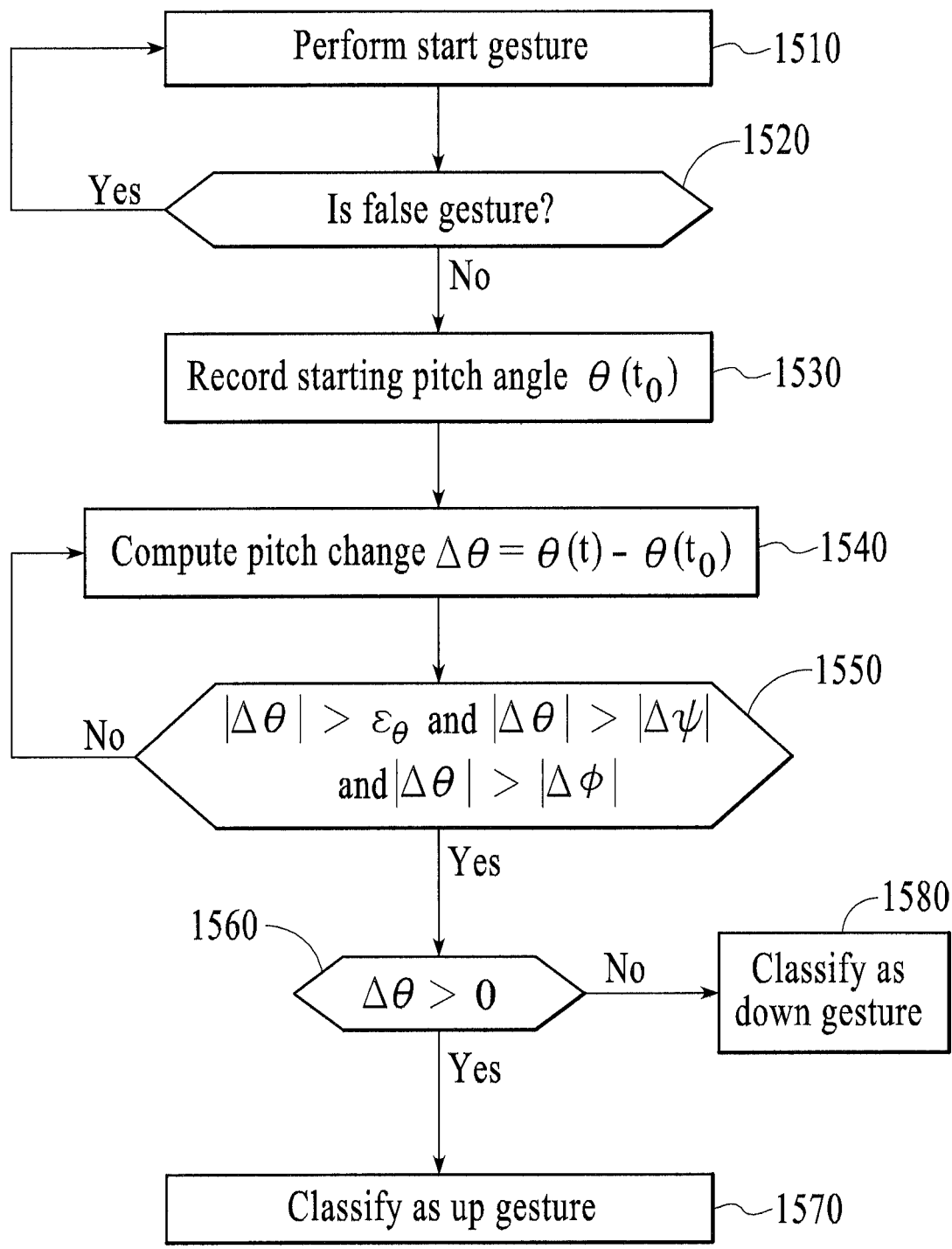
FIG. 15 illustrates a pitch gesture detection flowchart according to further embodiments.

FIG. 15 illustrates a pitch gesture detection flowchart according to further embodiments. Step 1510 indicates that the start gesture has been performed and detected, as previously described. Step 1520 follows, and a determination of whether the gesture that has been initiated is a true gesture or a false gesture is made. If a false gesture, then a reset is performed, such that determination processor sets another gesture start signal usable as the gesture start signal thereafter, and then the process continues. Assuming the gesture initiated is not a false gesture, then data relating to the pitch angle is detected in step 1530. Step 1540 then detects the change in pitch angle from the initial position. In step 1550, it is determined that the change in pitch angle, in absolute value, is greater than a threshold, and that the change in pitch angle is greater than the change in the yaw angle and the change in the roll angle. If the answer is no, then a return to step 1540 occurs, whereas if the answer is yes, then a determination as to the sign of the change in angle is determined, such that if greater than 0, it is classified as a right gesture in step 1570, and if not greater than 0, then it is classified as a left gesture in step 1580.

A false gesture, as referred to above, can be, for example, a different initial movement. For example, if the start signal is a hold on the auxiliary sensor, then a tap or a double tap could possibly be interpreted to mean a hold. In such cases, instead of re-starting the start gesture signal immediately thereafter, another hold on the auxiliary sensor is waited for until the start gesture signal is then made.

Also, the specific gesture thresholds are preferably based upon nominal classifications with no extreme motions, which can then be empirically derived based upon testing, typically of a number of different users, and with the particular sensor apparatus that is being used. Each of the above-mentioned specific gestures are preferably also associated with a nominal time scale, which is the time taken by a user to perform the gesture in nominal conditions. Angular tolerances as explained herein, represent the angular change that happens on the nominal time scale.

Further, the computation of the three euler angles will in most embodiments require data from an accelerometer, a gyroscope and a compass, which are all located on the same single sensing device, and the data from each of these are fused using a filter that provides some guarantee of optimality in terms of error or related metrics, as well as convergence guarantee. Such filters are Kalman filters, and complimentary filters, to name a few and as described above.

Each one of these sensors needs to be calibrated to account for possible errors, such as misalignment and effects of package stress. Also, for compass data, accounting for effects of environmental disturbances is a preferred approach.

Although the present inventions are described with respect to certain preferred embodiments, modifications thereto will be apparent to those skilled in the art.

The invention claimed is:

1. An apparatus capable of interacting with at least one controllable device based upon a pose of at least a portion of a human body, the apparatus comprising:
   one or more sensors that are sized for wearing on the human body, each of the one or more sensors emitting sensor data; and
   a detection unit that operates upon the sensor data to determine the pose of at least the portion of the human body and is capable of interacting with the at least one controllable device, the detection unit including:
      a memory that stores at least one or more characteristics of human anatomy that are associated with the human body using at least a partial skeletal rendering of a human; and
      a detection processor, automatically operating under software control, that inputs, aggregates and fuses the sensor data from each of the one or more sensors using the at least one or more characteristics of human anatomy stored in the memory to determine the pose of at least the portion of the human body based upon a locality of said one or more sensors, and wherein the pose is determined using at least a comparison of which one of an absolute value of a change in roll, a change in pitch and a change in yaw is greatest when compared to each other during a period of time.

2. The apparatus according to claim 1 further including an auxiliary sensor sized for wearing on the human body that receives a first specific input based on one of a tactile switch and capacitive touch input and generates a gesture start signal;
   and wherein the period of time is determined by when the detection processor begins to input, aggregate and fuse the sensor data upon receipt of the gesture start signal and ceases to input the sensor data upon receipt of a gesture stop signal; and
   wherein the auxiliary sensor receives a second specific input based on one of the tactile switch and the capacitive touch input and generates the gesture stop signal.

3. The apparatus according to claim 2 wherein the detection processor determines that the roll change is greatest, and that the roll change is greater than 0, thereby determining a clockwise gesture signal.

4. The apparatus according to claim 2 wherein the detection processor determines that the roll change is greatest, and that the roll change is less than 0, thereby determining a counter clockwise gesture signal.

5. The apparatus according to claim 2 wherein the detection processor determines that the yaw change is greatest, and that the yaw change is greater than 0, thereby determining a right gesture signal.

6. The apparatus according to claim 2 wherein the detection processor determines that the yaw change is greatest, and that the yaw change is less than 0, thereby determining a left gesture signal.

7. The apparatus according to claim 2 wherein the detection processor determines that the pitch change is greatest, and that the pitch change is greater than 0, thereby determining an up gesture signal.

8. The apparatus according to claim 2 wherein the detection processor determines that the pitch change is greatest, and that the pitch change is less than 0, thereby determining a down gesture signal.

9. The apparatus according to claim 2 wherein the detection processor determines that an initial movement is a false gesture, and sets another gesture start signal usable as the gesture start signal thereafter.

10. The apparatus according to claim 1, wherein the change in roll, the change in yaw, and the change in pitch are each determined based upon usage of an euler angle.

11. A method for interacting with at least one controllable device based upon a pose of at least a portion of a human body, the method comprising:
   sensing, using one or more sensors that are sized for wearing on the human body, sensor data from each of the one or more sensors; and
   determining the pose of at least the portion of the human body based upon the sensor data, under processor and software control, the step of determining operating to:
      associate at least one or more characteristics of human anatomy with the human body using at least a partial skeletal rendering of a human; and
      automatically determine, under the processor and software control the pose of at least the portion of the human body based upon a locality of said one or more sensors, the step of automatically determining including inputting, aggregating and fusing the sensor data from each of the one or more sensors using the at least one or more characteristics of human anatomy to determine the pose, wherein the pose is determined using at least a comparison of which one of an absolute value of a change in roll, a change in pitch and a change in yaw is greatest when compared to each other during a period of time.

12. The method according to claim 11, further including the steps of:
   sensing, using an auxiliary sensor sized for wearing on the human body a first specific input based on one of a tactile switch and capacitive touch input and generating a gesture start signal; and
   generating a gesture stop signal from the auxiliary sensor sized for wearing on the human body, the gesture stop signal obtained based upon a second specific input based on one of the tactile switch and the capacitive touch input, wherein the period of time is determined between the generation of the gesture start signal and the generation of the gesture stop signal.

13. The method according to claim 12 wherein the step of automatically detecting determines that the roll change is greatest, and that the roll change is greater than 0, thereby determining a clockwise gesture signal.

14. The method according to claim 12 wherein the step of automatically detecting determines that the roll change is greatest, and that the roll change is less than 0, thereby determining a counter clockwise gesture signal.

15. The method according to claim 12 wherein the step of automatically detecting determines that the yaw change is greatest, and that the yaw change is greater than 0, thereby determining a right gesture signal.

16. The method according to claim 12 wherein the step of automatically detecting determines that the yaw change is greatest, and that the yaw change is less than 0, thereby determining a left gesture signal.

17. The method according to claim 12 wherein the step of automatically detecting determines that the pitch change is greatest, and that the pitch change is greater than 0, thereby determining an up gesture signal.

18. The method according to claim 12 wherein the step of automatically detecting determines that the pitch change is greatest, and that the pitch change is less than 0, thereby determining a down gesture signal.

19. The method according to claim 12 wherein the step of automatically detecting determines that an initial movement is a false gesture, and sets another gesture start signal usable as the gesture start signal thereafter.

20. The method according to claim 12, wherein the change in roll, the change in yaw, and the change in pitch are each determined based upon usage of an euler angle.

* * * * *